United States Patent [19]
He et al.

[11] Patent Number: 5,792,739
[45] Date of Patent: Aug. 11, 1998

[54] LIQUID COMPOSITIONS COMPRISING HYDROPHOBICALLY MODIFIED POLYALKYLENE GLYCOLS AS MILDNESS ACTIVES

[75] Inventors: Mengtao He, Wayne; Michael Fair, Hackensack, both of N.J.; Michael Massaro, Congers, N.Y.

[73] Assignee: Lever Brothers Company, Division of Conopco, Inc., New York, N.Y.

[21] Appl. No.: 637,144

[22] Filed: Apr. 24, 1996

[51] Int. Cl.$^6$ .................... C11D 1/12; C11D 1/83
[52] U.S. Cl. .............. 510/422; 510/404; 510/421; 510/130
[58] Field of Search .................. 510/141, 152, 510/154, 155, 421, 422, 405, 130

[56] References Cited

U.S. PATENT DOCUMENTS

| | | | |
|---|---|---|---|
| 4,247,425 | 1/1981 | Egan et al. | 252/152 |
| 4,256,611 | 3/1981 | Egan et al. | 252/547 |
| 4,343,726 | 8/1982 | Egan et al. | 252/548 |
| 4,828,750 | 5/1989 | Simion et al. | 252/548 |
| 5,520,840 | 5/1996 | Massaro et al. | 252/174.17 |
| 5,540,854 | 7/1996 | Fair et al. | 510/152 |
| 5,543,072 | 8/1996 | Fost et al. | 510/151 |

FOREIGN PATENT DOCUMENTS

| | | |
|---|---|---|
| 4409189 | 3/1994 | Germany . |
| 1330148 | 12/1988 | U.S.S.R. . |
| 2288811 | 11/1995 | United Kingdom . |
| 2288812 | 11/1995 | United Kingdom . |
| 94/23695 | 4/1993 | WIPO . |

*Primary Examiner*—Paul Lieberman
*Assistant Examiner*—Necholus Ogden
*Attorney, Agent, or Firm*—Ronald A. Koatz

[57] ABSTRACT

The present invention relates to liquid detergent compositions comprising anionic/amphoteric surfactant systems. Low addition levels of specific hydrophobically modified polyalkylene glycol wherein ratio of hydrophobically modified polyalkylene glycol to anionic surfactant is defined have been found to remarkably enhance mildness without sacrificing processibility and desired user properties. In a second embodiment, the invention relates to a method for enhancing mildness in liquid detergent compositions comprising anionic surfactant by adding said defined hydrophobically modified polyalkylene glycols.

7 Claims, 3 Drawing Sheets

LIQUID COMPOSITIONS COMPRISING HYDROPHOBICALLY MODIFIED POLYALKYLENE GLYCOLS AS MILDNESS ACTIVES

FIELD OF THE INVENTION

The present invention relates to liquid personal wash compositions (e.g., shower gels), particularly, to compositions comprising (1) one or more anionic surfactants and (2) one or more amphoteric surfactants. Specifically, the invention relates to the incorporation of relatively low addition levels of specific hydrophobically modified polyalkylene glycols (HMPEG) in the liquids. Through careful balancing of anionic surfactant to HMPEG and specific selection of the HMPEG, enhanced mildness is obtained without sacrificing processability, lather performance and other desired user properties.

BACKGROUND

The use of hydrophobically modified polyalkylene glycols in liquid personal wash compositions is not new. High molecular weight hydrophobically modified polyalkylene glycols (HMPEG) have been used previously as thickeners in liquids at an addition level of less than 5% wt. of total composition; beyond this level, over-thickening can be induced. Some prior art (e.g., Patents by Egan et al. discussed below) teach that only relatively high levels of addition of HMPEG (HMPEG to anionic surfactant weight ratio between 1:1 and 4:1) can effectively reduce the skin irritation potential of anionic surfactants. However, this high levels of HMPEG can cause over-thickening, and the referred patents also teach the solution to control the viscosity. Two GB patent application by Dias et al. teach that the combination of urea, alpha- or beta-hydroxy acid, and animal/oil derived ethoxylated nonionic surfactants (some of them are the HMPEG of the subject invention) are needed to achieve desired skin feel effect.

The references are discussed below.

Patent No. WO 9,423,695 to Unilever NV teaches a personal washing formulation that contains 3–15% sodium lauryl (EO) sulfate, 3–10% sulphosuccinate surfactants, 0.5–3% thickener such as fatty acid glyceride polyglycol ether (a HMPEG), and 0.1–5% of an emulsifier such as PEG 40 hydrogenated castor oil. The percentage of the fatty acid glyceride polyglycol ether is outside the range of choice of our invention, and the molecular weight of PEG 40 hydrogenated castor oil is below 4000, which is also outside the range of choice of our invention.

Patent No. SU 1,330,148 to S. Navardausk, R. Zilberman, and D. Kurdyumova teaches a liquid cleanser formulation containing 2–4 % wt. of polyethylene glycol ester of 10–16 C (a HMPEG) as thickener mixed with other ingredients. The percentage of the 10–16 C polyethylene glycol ester in total composition is below 5%, which is outside the range of choice of our invention.

Patent No. DE 4,409,189 to Chem-Y Chem Fab GMBH teaches a surfactant composition containing 5–20% anionic surfactants, 2.5–10% alkyl polyglucoside, 1–4% ethoxylated rape seed oil fatty acid (can be a HMPEG), and 0.5–2.5% polyoxyethylene propylene dioleate (a HMPEG) as thickener. The percentage of the HMPEG in total composition is outside the range of choice of our invention.

Patent No. FR 2,336,475 to Gillette Co. teaches the use of amphoteric surfactant and nonionic surfactant as major actives and anionic surfactant as coactives in a PW liquid. The formulation contains 2% thickener such as polyethylene glycol 6000 distearate (a HMPEG). The percentage of the HMPEG in total composition is outside the range of choice of our invention.

U.S. Pat. No. 4,828,750 to F. Simion, L. Rhein, J. Blake-Haskins, S. Babulak and R. Cantore teaches a formulation containing 0.25–6% nonionic surfactant, 0.05–5% of an organic acid, 0.1–4% of a thickening agent, such as a diester of stearic acid and polyoxyethylene (can be a HMPEG of the subject invention). The level of the diester of stearic acid and polyoxyethylene is below 5% by wt. total composition, which is outside the range of choice of our invention.

U.S. Pat. Nos. 4,247,425, 4,343,726, and 4,256,611 to R. Egan teach liquid skin cleansing formulations containing anionic surfactant and hydrophobically modified polyalkylene glycols (e.g., POE(200)-glyceryl-stearate) as mildness enhancers. These patents showed that only at relatively high addition level of the hydrophobically modified polyalkylene glycols (hydrophobically modified polyalkylene glycols/anionic surfactant weight ratio above 1:1 (preferably 1:1 to 4:1)), the hydrophobically modified polyalkylene glycols can significantly reduce the irritation of anionic surfactant. However, use of high levels of HMPEG may thicken the liquid composition and require extra efforts to control the viscosity of the formulation, which is part of the art of this invention.

UK Patent Application Nos. GB 2,288,811A and GB 2,288,812A to L. Dias, M. Giret, C. Leahy, and R. Elliot teach liquid skin cleansing formulations containing 5 to 50% of anionic, amphoteric and zwitterionic surfactants in general, 0.1 to 20% of a soluble or dispersible nonionic surfactant selected from ethoxylated animal and vegetable oils and fats and mixtures thereof, 0.5–8% urea, and 0.1–5% alpha or beta hydroxy acid. Evidently, the art of this invention is to use a combination of urea, the animal/vegetable oil derived ethoxylated nonionic surfactants (some of them can be the HMPEG of the subject invention), and hydroxy acid to achieve desirable skin feel and mildness (PG11, Line 4 to 6, and PG4, Line 26 to 28). However, neither in-vivo nor in-vitro data were presented to support the mildness claim, and no anionic/ethoxylated nonionic weight ratio was specified in these applications. Finally, the references require a specific combination of ingredients (e.g., urea and the oil-fat derived ethoxylated nonionic surfactants) to achieve the desired skin feel effects, thus use of urea is a criticality. In contrast, the use of urea is not required in the subject invention, and, in fact, is specifically disclaimed.

The subject invention differs from the prior art referred above, alone or in combination, in that the applicants have found that at relatively low levels, defined hydrophobically modified polyalkylene glycols (e.g., having specific HMPEG to anionic surfactant weight ratio below 1:1, specific range of molecular weight, and specific ethylene oxide: hydrophobe ratio) in specific surfactant systems (e.g., containing greater than or equal to 50% anionic surfactant(s); and also necessarily containing at least some amphoteric surfactant) will result in enhanced mildness of the specific systems without sacrificing processibility and user properties. Additionally, the low levels of addition of HMPEG avoids the problem of over-thickening and can reduce the cost of the liquid compositions.

BRIEF SUMMARY OF THE INVENTION

Unexpectedly, applicants have found that in liquid personal wash compositions comprising a surfactant system comprising:

(1) 3% to 30% by wt., preferably 5% to 20%, total composition anionic surfactant or mixture of anionic surfactants, wherein anionic is greater than or equal to 50% of the surfactant system; and (2) 0.1 to 20% by wt. total composition one or more amphoteric surfactants;

(3) the addition of 5 to 25% by wt. (preferably 5 to 15%) of total composition of hydrophobically modified polyalkylene glycols (HMPEG) wherein weight of alkylene oxide (e.g., ethylene oxide) portion is between 60% and 90%, preferably 85% to 97% wt. of the weight of the HMPEG, will lead to significantly enhanced mildness in such compositions without sacrificing processibility and desired user properties, such as rich and creamy lather.

Weight ratio of HMPEG to anionic surfactant is between 1:1.1 to 1:10. This ratio is a criticality because above the range of this ratio, special efforts have to be made to control the high viscosity of liquid personal wash compositions, and the cost of the composition can be raised; below this range, skin irritation potential of anionic surfactant can not be effectively mitigated.

The HMPEG should have molecular weight of 4,000 to 25,000, preferably 4,000 to 15,000. This MW range is a criticality because, above this range of molecular weight, HMPEG can cause over-thickening and cause processing and handling difficulties. Below this MW range, HMPEG approaches the structure of a conventional ethoxylated nonionic detergent and may impair lather performance and other desired user properties.

DETAILED DESCRIPTION OF THE INVENTION

Figure 1A:
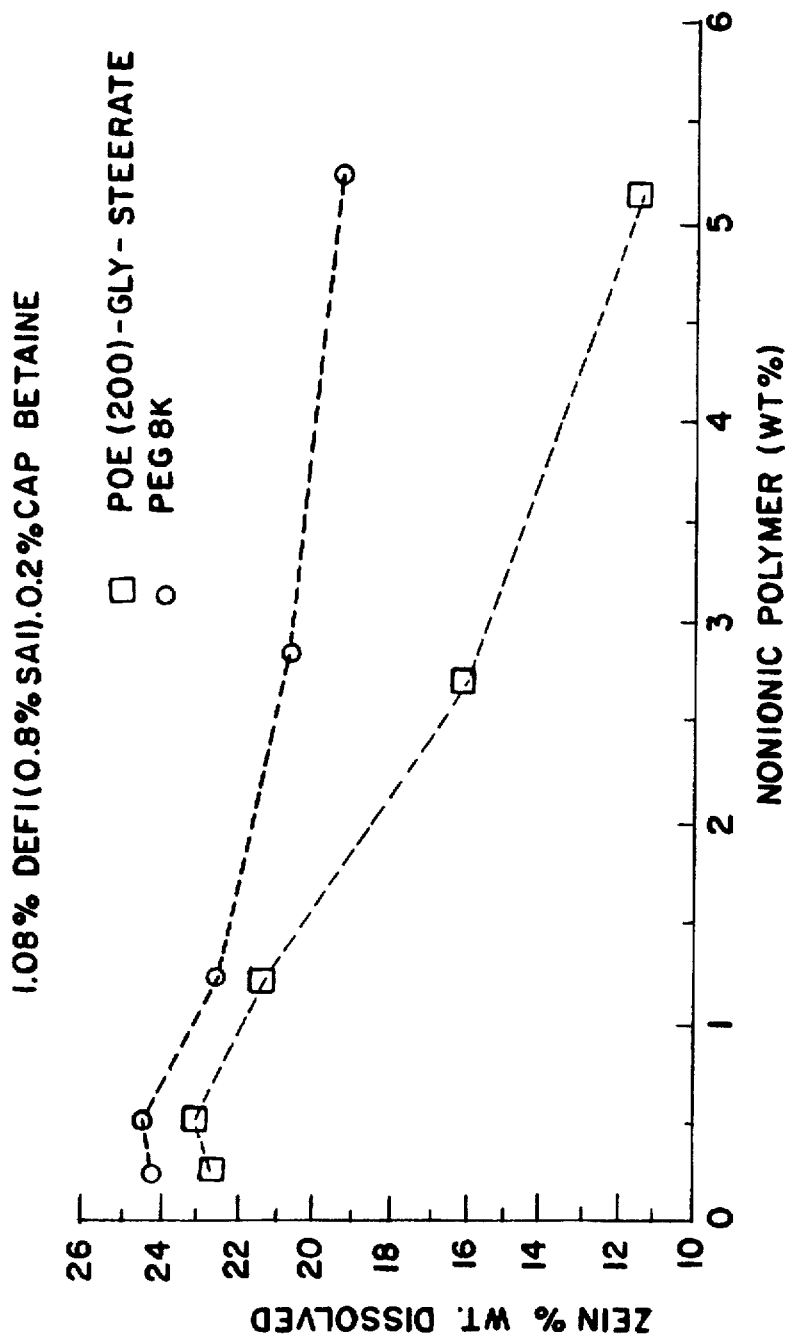
FIG. 1a and FIG. 1b show the Zein % dissolved by acyl isethionate/cocoamido propyl betaine as a function of nonionic polymeric surfactant concentration. In contrast to PEG 8000, POE(200) glyceryl stearate and POE(200) glyceryl tallowate significantly reduced the Zein % dissolved at relatively low levels. Therefore the irritation potential of a personal washing bar can be further reduced by including relatively low levels (i.e. less than 30%) of defined hydrophobically modified polyalkylene glycols in a full liquid composition.

The present invention relates to novel liquid personal water compositions, particularly compositions in which the surfactant system comprises greater than 50% of the surfactant system anionic surfactant or surfactants, and additionally comprises one or more amphoteric surfactants.

Unexpectedly, applicants have found that when relatively small amounts (5 to 25% by wt. composition) of a defined hydrophobically modified polyalkylene glycols (i.e., defined by MW of 4,000-25,000; by percentage of EO of the polymer being between 60% and 99% wt.;) is used, and when there is a defined ratio of the hydrophobically modified polymer to anionic surfactant (i.e., 1:1.1 to 1:10), the liquid composition is significantly milder (as defined by zein dissolution and patch tests) than either in the absence of the polymer or if a different alkylene oxide (e.g., polyethylene oxide) is used.

The compositions are defined in greater detail below:

Surfactant System

The surfactant system of the subject invention generally comprises 5 to 50% by weight, preferably 10 to 40% by wt. of the composition and comprises:

(a) 3% to 30%, preferably 5 to 20% by wt. total composition one or more anionic surfactants wherein the anionic surfactant comprises 50% or more of the surfactant system;

(b) 0.1 to 20% by wt., preferably 3% to 10% total composition amphoteric and/or zwitterionic surfactant; and (c) 0% to 10% optional nonionic surfactant (other than hydrophobically modified polyalkylene glycols of invention).

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

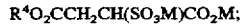

$$R^4O_2CCH_2CH(SO_3M)CO_2M;$$

amido-MEA sulfosuccinates of the formula

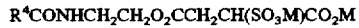

$$R^4CONHCH_2CH_2O_2CCH_2CH(SO_3M)CO_2M$$

wherein $R^4$ ranges from $C_8$–$C_{22}$ alkyl and M is a solubilizing cation;

amido-MIPA sulfosuccinates of formula

$$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R-O-(CH_2CH_2O)_nCCH_2CH(SO_3M)CO_2M$$
(with carbonyl O above the C)

wherein n=1 to 20; and M is as defined above.

Sarcosinates are generally indicated by the formula

$$RCON(CH_3)CH_2CO_2M,$$

wherein R ranges from $C_8$–$C_{20}$ alkyl and M is a solubilizing cation.

Taurates are generally identified by formula $$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R—(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

$$\begin{array}{ccc} O & X & Y \\ \parallel & | & | \\ RC-O-CH-CH_2-(OCH-CH_2)_m-SO_3M^+ \end{array}$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the anionic component will comprise from about 1 to 20% by weight of the composition, preferably 5 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$\begin{array}{c} (R^3)_x \\ | \\ R^2-Y^{(+)}-CH_2-R^4Z^{(-)} \end{array}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl) ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$\begin{array}{ccc} O & & R^2 \\ \parallel & & | \\ R^1+C-NH(CH_2)_n\frac{1}{m}N^+-X-Y \\ & & | \\ & & R^3 \end{array}$$

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $—CO_2—$ or $—SO_3—$ Suitable amphoteric detergents within the above general formula include simple betaines of formula:

$$\begin{array}{c} R^2 \\ | \\ R^1-N^+-CH_2CO_2^- \\ | \\ R^3 \end{array}$$

and amido betaines of formula:

$$\begin{array}{c} R^2 \\ | \\ R^1-CONH(CH_2)_m-N^+-CH_2CO_2^- \\ | \\ R^3 \end{array}$$

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

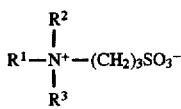

or

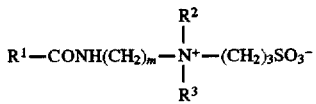

where m is 2 or 3, or variants of these in which —(CH$_2$)$_3$SO$^-$$_3$ is replaced by

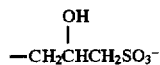

In these formulae R$^1$, R$^2$ and R$^3$ are as discussed previously.

A further possibility is that the amphoteric detergent is a sulphobetaine of formula

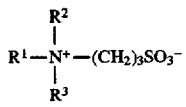

or

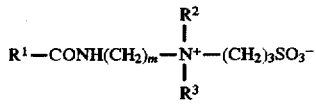

where m is 2 or 3, or variants of these in which —(CH$_2$)$_3$SO$_3^-$ is replaced by

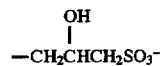

In these formulae R$^1$, R$^2$ and R$^3$ are as discussed previously.

Amphoacetates and diamphoacetates are also intended to be covered in possible zwitterionic and/or amphoteric compounds which may be used.

The amphoteric/zwitterionic generally comprises 0.1 to 20% by weight, preferably 0.1% to 15%, more preferably 0.1 to 10% by wt. of the composition.

In addition to one or more anionic and amphoteric and/or zwitterionic, the surfactant system may optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl (C$_6$–C$_{22}$) phenols-ethylene oxide condensates, the condensation products of aliphatic (C$_8$–C$_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

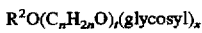

wherein R$^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

Hydrophobically Modified Polyalkylene Glycols (HMPEG)

The hydrophobically modified polyalkylene glycols (HMPEG) of the subject invention are generally commercially available nonionic polymeric surfactants having a broad molecular weight range from about 4000 to 25000 (preferably 4000 to 15000). This range of molecular weight is a criticality because, above the defined range of molecular weight, HMPEG can make liquid formulations sticky and viscous, which causes processing problems, such as difficulties in mixing and handling. Below this range, HMPEG approaches the structure of a conventional nonionic detergent that may impair lather performance and desired user properties.

Generally, the polymers will be selected from alkylene nonionic polymers chemically and terminally attached by hydrophobic moieties, wherein the hydrophobic moiety can be derivatives of linear or branched alkyl, aryl, alkylaryl, alkylene, acyl (e.g., having a carbon number of C4 to C40); fat and oil derivatives of alkylglyceryl, glyceryl, sorbitol, lanolin oil, coconut oil, jojoba oil, castor oil, almond oil, peanut oil, wheat germ oil, rice bran oil, linseed oil, apricot pits oil, walnuts, palm nuts, pistachio nuts, sesame seeds, rapeseed, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, etc. These hydrophobically modified polyalkylene glycols are usually commercially available (see Table 1 for examples).

To ensure water solubility, it is preferred that the portion of ethylene oxide moiety per mole of HMPEG is between 60% wt. and 99% wt. (preferably 85% wt. to 97% wt.). In other words, the total content of the hydrophobic moiety is between 1% wt. and 40% wt. (preferably 3% wt. to 15% wt.) per mole of the defined HMPEG.

Specifically, examples of various hydrophobically modified polyalkylene glycols are set forth in Table 1 below where in T$_m$ (°C.) were obtained from literature from the corresponding chemical suppliers or measured by the inventors using a differential scanning calorimetry technique.

TABLE 1

Representative hydrophobically modified PEGs.
(R = hydrophobic moieties such as linear or branched alkyl chains
(e.g., having carbon number of C4 to C40); derivatives of sorbitol,
lanolin radical, coconut radical, jojoba acid radical, castor oil radical,
etc.; POE = Polyoxyethylene (e.g., —(CH$_2$CH$_2$O)$_m$H);
m = No. ethylene oxide monomer units; m > 50.)

| | | |
|---|---|---|
| POE(m)-R | Witco (Varonic LI-420) | R = glyceryltallowate; m = 200; white solid. |
| | Seppic (Simusol 220TM) | R = glycerylstearate; m = 200; white solid. |
| | Amerchol (Glucam E-200) | R = glucoside; m = 200; white water soluble; white solid. |
| | Calgene Chemical (600-S) | Tm: 52–62C; R = stearate; m = 150; Tm: 52–62C |
| | Calgene Chemical (600-L) | R = laurate; m = 150. |
| R-POE(m)-R | Stepan (KESSCO PEG6000 distearate) | R = stearate; m = 174; Tm: 54C; white solid. |

As noted, melting temperature of the compounds is preferred to be about 25°–85°.

In addition, the weight ratio of hydrophobically modified polyalkylene glycol to anionic surfactant should be in the range of 1:1.1 to 1:10. While not wishing to be bound by theory, this ratio is believed critical because, at ratios below 1:10, improvement on mildness is not significant and, at ratios above 1:1.1, special efforts have to be made to adjust the high viscosity of liquid wash compositions (see the prior art in U.S. Pat. No. 4,247,425, U.S. Pat. No. 4,343,726, and U.S. Pat. No. 4,256,611).

The defined hydrophobically modified polyalkylene glycols generally comprise 5 to 25% by wt. (preferably 5 to 15% by wt) of the total liquid composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, TiO$_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330— Polyquaternium 39; and Jaguar® type conditioners.

Polyethylene glycols which may be used include:

| | | |
|---|---|---|
| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut shells and apricot seeds.

The compositions may also contain 0.1 to 15% by wt., preferably 1 to 10% by wt. of a structurant. Such structurants can be used to avoid addition of external structurants (e.g., cross linked polyacylates and clays) if suspending particles is desired as well as to provide desirable consumer attributes.

The structurant is generally an unsaturated and/or branched long chain ($C_8$–$C_{24}$) liquid fatty acid or ester derivative thereof; and/or unsaturated and/or branched long chain liquid alcohol or ether derivatives thereof. It may also be a short chain saturated fatty acid such as capric acid or caprylic acid. While not wishing to be bound by theory, it is believed that the unsaturated part of the fatty acid of alcohol or the branched part of the fatty acid or alcohol acts to "disorder" the surfactant hydrophobic chains and induce formation of lamellar phase.

Examples of liquid fatty acids which may be used are oleic acid, isostearic acid, linoleic acid, linolenic acid, ricinoleic acid, elaidic acid, arichidonic acid, myristoleic acid and palmitoleic acid. Ester derivatives include propylene glycol isostearate, propylene glycol oleate, glyceryl isostearate, glyceryl oleate and polyglyceryl diisostearate.

Examples of alcohols include oleyl alcohol and isostearyl alcohol. Examples of ether derivatives include isosteareth or oleth carboxylic acid; or isosteareth or oleth alcohol.

The structuring agent may be defined as having melting point below about 25° C. centigrade.

Another optional ingredient is oil/emollient which may be added as a benefit agent to the liquid compositions.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acytylated lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, silicone oil such as dimethyl polysiloxane, lauryl and myristyl lactate.

It should be understood that where the emollient may also function as a structurant, it should not be doubly included such that, for example, if the structurant is 15% oleyl alcohol, no more than 5% oleyl alcohol as "emollient" would be added since the emollient (whether functioning as emollient or structurant) should not comprise more than 20%, preferably no more than 15% of the composition.

The emollient/oil is generally used in an amount from about 1 to 20%, preferably 1 to 15% by wt. of the composition. Generally, it should comprise no more than 20% of the composition.

The following examples are intended to illustrate further the invention and are not intended to limit the invention in any way.

All percentages are intended to be percentages by weight unless stated otherwise.

EXAMPLES

Protocol

Mildness Assessments

Zein dissolution test was used to preliminary screen the irritation potential of the formulations studied. In an 8 oz. jar, 30 mLs of an aqueous dispersion of a formulation were prepared. The dispersions sat in a 45° C. bath until fully dissolved. Upon equilibration at room temperature, 1.5 gms of zein powder were added to each solution with rapid stirring for one hour. The solutions were then transferred to centrifuge tubes and centrifuged for 30 minutes at approximately 3,000 rpms. The undissolved zein was isolated, rinsed and allowed to dry in a 60° C. vacuum oven to a constant weight. The percent zein solubilized, which is proportional to irritation potential, was determined gravimetrically.

The Protocol of 3-Day Patch Test

Patch test was used to evaluate skin mildness of aqueous dispersions containing 1% DEFI active (sodium cocoyl isethionate) and different levels of the structurant/coactives. Patches (Hilltop® Chambers, 25 mm in size) were applied to the outer upper arms of the panelists under bandage type dressings (Scanpor® tape). After each designated contact periods (24 hrs. for the first patch application, 18 hrs. for the second and third applications), the patches were removed and the sites were visually ranked in order of severity (erythema and dryness) by trained examiners under consistent lighting.

Formulation Processing

Formulations shows in the examples of this invention were prepared in 400 mL beakers in a 40°–60° C. oil bath. Mixing was accomplished with a variable speed overhead motor. Batch size was varied from 100–250 gms. All chemicals used were commercial materials and used as supplied. Those chemicals were dispersed in Milli-Q water, which accounted for 50–80% of the whole formulation. After the batch was homogeneously mixed, it was allowed to be cooled under room temperature.

Example 1

Figure 1B:
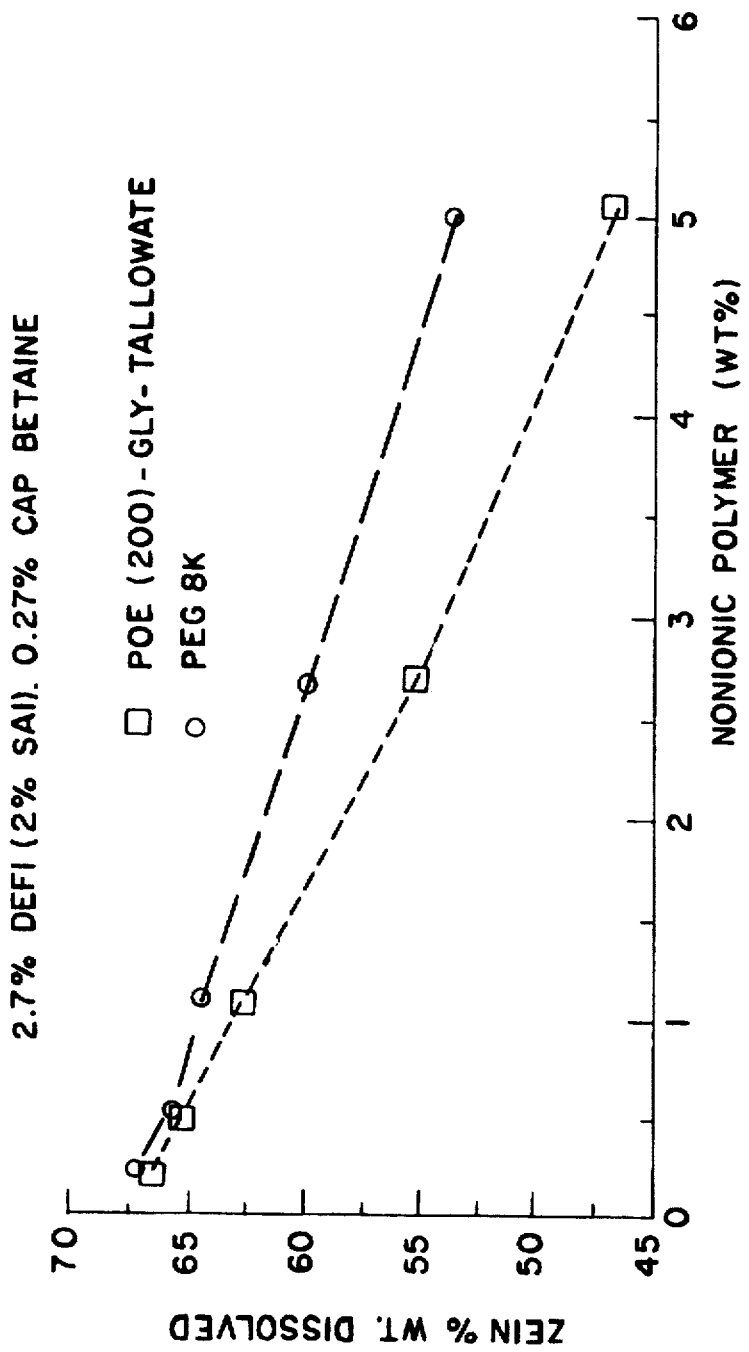

The irritation reduction potential of hydrophobically modified polyalkylene glycols was investigated using Zein dissolution experiments. As indicated in FIG. 1a and FIG. 1b, the defined hydrophobically modified polyalylene glycols (HMPEG), as a class, are significantly more effective than PEG in reducing the Zein % dissolved by 1% to 2.7% aqueous DEFI suspension (DEFI is a sodium acyl isethionate/fatty acid mixture defined in the Table 2 of Example 3). The data in FIG. 1a and FIG. 1b also showed that at relatively low level of addition of HMPEG (HMPEG to anionic surfactant weight ratio below 1:1), HMPEG significantly reduced the amount of Zein dissolved by DEFI.

Example 2

Figure 2:
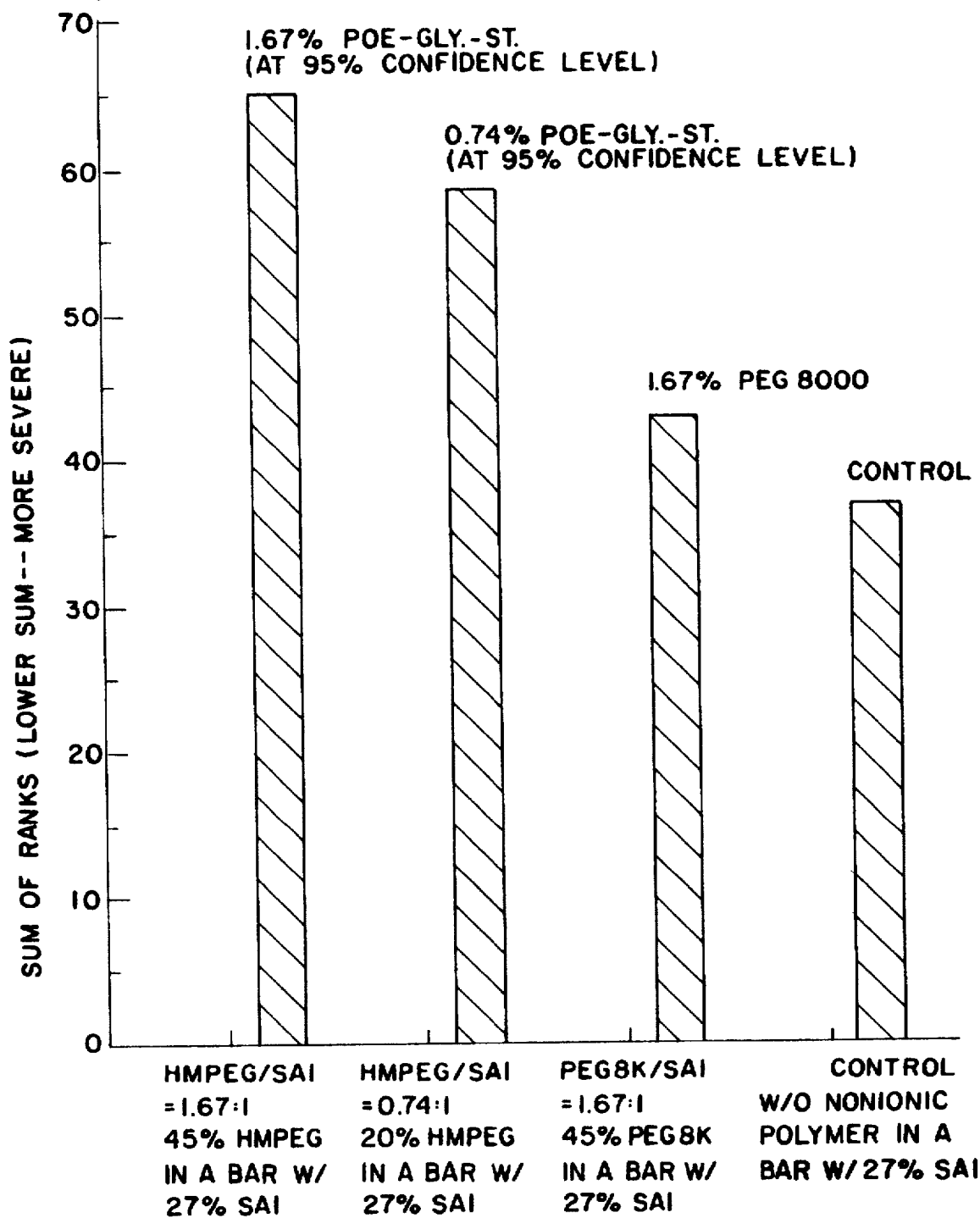
FIG. 2 shows that, even at relatively low levels of addition, a HMPEG of the invention (POE(200) glyceryl stearate) significantly reduces skin irritation caused by sodium acyl isethionate.

Three day skin patch tests showed that, even at low levels of addition, POE(200) glyceryl stearate significantly reduced the skin irritation caused by even a mild surfactant system, such as sodium acyl isethionate/cocoamido propyl betaine. As shown in FIG. 2, at a POE(200) glyceryl stearate to sodium acyl isethionate (SAI) weight ratio around 0.74:1 (equivalent to 10% wt. POE(200) glyceryl stearate in a liquid containing 13.5% wt. sodium acyl isethionate), POE (200) glyceryl stearate reduced the skin irritation of a DEFI/betaine liquor significantly. In contrast, even at a PEG 8000 to SAI weight ratio as high as 1.67:1 (effectively 22.5% wt. PEG 8000 in a liquid with 13.5% SAI), PEG 8000 made no measurable mildness contribution to the SAI/CAP betaine aqueous liquor.

Example 3

All amounts are given in percentage of weight. These formulations used sodium cocoyl isethionate as the major anionic detergent with other amphoteric and anionic surfactants as coactives. The formulation (A) was a stable milky white cream, which provided rich, creamy, and slippery lather that was rinsed off easily. The formulation (B) and (C) were stable milky white lotions that were pourable and pumpable. These lotions provided rich and creamy lather.

TABLE 2

| Formulation | (A) | (B) | (C) |
|---|---|---|---|
| Sodium cocoyl isethionate (From DEFI*) | 0 | 0 | 14.5% |
| Sodium cocoyl isethionate (From IGEPON AC-78) | 10.0% | 9.0% | 0.0 |
| Cocoamidopropyl betaine | 5.0 | 4.5 | 3.8 |
| Sodium lauryl ether sulphate, 3EO | 0.0 | 1.8 | 4.8 |
| Glycerin | 0.0 | 1.4 | 1.0 |
| Palmitic-stearate acid (From IGEPON or DEFI) | 0.4 | 0.4 | 4.5 |
| POE(200) glyceryl stearate | 5.0 | 0.0 | 6.0 |
| POE(200) glyceryl tallowate | 0.0 | 7.0 | 0.0 |
| Propylene glycol | 0.0 | 4.8 | 0.0 |
| Sodium chloride | 2.0 | 1.8 | 1.4 |
| Ammonium chloride | 0.0 | 5.8 | 5.0 |
| Sodium isethionate | 0.4 | 0.4 | 0.2 |
| Water | balance to 100% | balance to 100% | balance to 100% |

*DEFI: directly esterified fatty acid isethionate, which is a mixture containing about 74% by weight of sodium acyl isethionate, 23% stearic-palmitic acid and small amounts of other materials, manufactured by Lever Brothers Co, U.S.

Example 4

All amounts are given in percentage of weight. These formulations used sodium lauryl sulphate, (3EO) as the major anionic detergent with optional amphoteric and anionic surfactants as coactives. These clear, pourable liquids provided rich, creamy and slippery lather and smooth skin feel.

TABLE 3

| Formulation | (C) | (D) | (E) |
|---|---|---|---|
| SLES (3EO) | 5.0 | 10.0 | 15.0 |
| Sodium lauryl | 5.0 | 3.0 | 0.0 |

TABLE 3-continued

| Formulation | (C) | (D) | (E) |
|---|---|---|---|
| sarcosinate | | | |
| Cocoamido-propyl betaine | 5.0 | 5.0 | 10.0 |
| Propylene glycol | 2.0 | 1.0 | 2.0 |
| POE(200) glyceryl stearate | 5.0 | 10.0 | 10.0 |
| Water | Balance to 100% | Balance to 100% | Balance to 100% |

We claim:

1. A liquid detergent composition comprising:
   (a) a detergent surfactant system comprising:
      (1) 3% to 30% by wt. total composition anionic or mixtures of anionic surfactants wherein the anionic surfactant comprises 50% or greater of the detergent active system; and
      (2) 0.1% to 20% by wt. total composition comprising one or more amphoteric surfactants, and
   (b) 5 to 25% by wt. of a polyalkylene glycol polymeric surfactant having the structure:

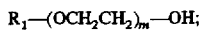

$R_1-(OCH_2CH_2)_m-OH$;

or

$R_1-(OCH_2CH_2)_m-OR_2$ wherein:
   m is greater than about 150;
   $R_1$ and $R_2$ are independently selected form the group consisting of $C_4$ to $C_{40}$ linear or branched alkyl, acyls, aryls, alkaryls, alkenyls and fat and oil derivatives thereof; and
   portion of $R_1$ and/or $R_2$ in each mole of the structure is between 1% and 40% by wt. of the structure;
   wherein the ratio of polyalkylene glycol to anionic or anionics is 1:1.1 to 1:10; and
   wherein the polyalkylene glycol is further defined by having a molecular weight of 4,000 to 25,000 Dalton; having a weight percentage of alkylene oxide comprising the polymer between 60% and 99%; and having a melting temperature of 25° C. to 85° C.

2. A composition according to claim 1(a), wherein the anionic surfactant or surfactants comprises 5% to 20% of the composition.

3. A composition according to claim 1(a), wherein amphoteric comprises 3% to 10% of the composition.

4. A composition according to claim 1(b), wherein weight ratio of polyalkylene glycol to anionic surfactants is between 1:1.1 to 1:7.

5. A composition according to claim 1(b), wherein alkylene oxide comprises 85% to 97% by wt. of the polyalkylene glycol.

6. A composition according to claim 1(b), wherein MW of the polyalkylene glycol is between 4,000 to 15,000 Dalton.

7. A method of enhancing mildness of a liquid detergent composition comprising a surfactant system comprising 3% to 30% by wt. anionic or mixture of anionics which method comprises adding 5 to 25% by wt. of a polyalkylene glycol polymeric surfactant to said composition having the following structure:

$R_1-(OCH_2CH_2)_m-OH$;

or

$R_1-(OCH_2CH_2)_m-OR_2$ wherein:
m is greater than about 150;
$R_1$ and $R_2$ are independently selected form the group consisting of $C_4$ to $C_{40}$ linear or branched alkyl, acyls, aryls, alkaryls, alkenyls and fat and oil derivatives thereof; and
portion of $R_1$ and/or $R_2$ in each mole of the structure is between 1% and 40% by wt. of the structure;
wherein the ratio of polyalkylene glycol to anionic or anionics is 1:1.1 to 1:10; and
wherein the polyalkylene glycol is further defined by having the percentage of alkylene oxide comprising the polyalkylene glycol between 60% and 99%; and having a molecular weight of 4,000 to 25,000 Dalton.

* * * * *